United States Patent [19]

Rice et al.

[11] Patent Number: 4,788,222

[45] Date of Patent: Nov. 29, 1988

[54] METHOD FOR THE PRODUCTION OF HYDROCARBONS USING IRON-CARBON-BASED CATALYSTS

[75] Inventors: Gary W. Rice, Scotch Plains; Rocco A. Fiato, Basking Ridge; Stuart L. Soled, Pittstown, all of N.J.

[73] Assignee: Exxon Research and Engineering Company, Florham Park, N.J.

[21] Appl. No.: 38,637

[22] Filed: Apr. 15, 1987

Related U.S. Application Data

[63] Continuation-in-part of Ser. No. 735,768, May 20, 1985, Pat. No. 4,659,681, and a continuation-in-part of Ser. No. 735,769, May 20, 1985, Pat. No. 4,668,647.

[51] Int. Cl.$^4$ ................................................ C07C 1/04
[52] U.S. Cl. .................................... 518/700; 518/713; 518/717; 518/719; 518/721
[58] Field of Search ............... 518/700, 713, 717, 719, 518/721

[56] References Cited

U.S. PATENT DOCUMENTS

| | | | |
|---|---|---|---|
| 4,468,474 | 8/1984 | Gupta et al. | 502/5 |
| 4,518,707 | 5/1985 | Soled et al. | 518/717 |
| 4,548,953 | 10/1985 | Fiato et al. | 518/717 |

OTHER PUBLICATIONS

Hall et al., J. Soc. Chem. Ind. London 65, 128 (1946).
Weller, J. Am. Chem. Soc. 69, 2432 (1947).
Kummer et al., J. Am. Chem. Soc. 70, 3632 (1948).
SPIE 458, Appl. of Lasers to Industrial Chemistry, 131–139 (1984).
Catal. Rev.–Sc. Engr. 21, 1980 p. 225 (Kolbel, Ralek).
Gilbert, A. G., Sulzmann, K. G. P., *J. Electrochem. Soc.*, 1974, 121 832–834.

*Primary Examiner*—Howard T. Mars
*Attorney, Agent, or Firm*—Deborah L. Mellott

[57] ABSTRACT

This invention relates to a promoted finely divided or supported iron carbide-based catalyst which is produced by a gas phase pyrolytic decomposition reaction driven by a laser and the use of such a catalyst to produce various heavier hydrocarbons from CO and $H_2$.

22 Claims, 1 Drawing Sheet

METHOD FOR THE PRODUCTION OF HYDROCARBONS USING IRON-CARBON-BASED CATALYSTS

CROSS-REFERENCE TO RELATED APPLICATIONS

This application is a continuation-in-part of U.S. Ser. Nos. 735,768 and 735,769, both filed May 20, 1985 now U.S. Pat. Ser. Nos. 4,659,881 and 4,668,647.

FIELD OF THE INVENTION

This invention relates to a promoted finely divided or supported carbide-based catalyst which is produced by a gas phase pyrolytic decomposition reaction driven by a laser and the use of such a catalyst to produce various hydrocarbons, typically paraffin waxes and olefins, from CO and $H_2$.

BACKGROUND OF THE INVENTION

The Fischer-Tropsch reaction involves the catalytic hydrogenation of carbon monoxide to produce a variety of products ranging in size and functionality from methane to higher alcohols. The methanation reaction was first described by Sabatier and Senderens in 1902. The later work of Fischer and Tropsch dealing with higher hydrocarbons was described in Brennstoff-Chem., 7, 97 (1926).

The reaction is highly exothermic and care must be taken to design reactors for adequate heat exchange capacity. Nevertheless, substantial research has been undertaken in the interim since the initial characterization of the reaction during the 1920's. The process is especially suitable for use when carbonaceous feedstocks of otherwise low economic value are available. For instance, the first major commercial use of the Fischer-Tropsch process was in Germany during the mid-1930's. By the beginning of World War II, Germany was producing nearly 11,000 B/D of primary products using mainly the cobalt-based catalyst described by Fischer and Pichler (German Pat. No. 731,925—issued Aug. 2, 1936). The feedstock was, in general, based on available coals.

Subsequently, a consortium of nine American companies designed and built a plant at Brownsville, Tex. based on an iron-based catalyst. The plant was completed in 1950 and had a design capacity of 50MMSCFD. Various economic and technical difficulties caused final shutdown of the plant in the late 1950's.

A reasonably economic use of the process has been practiced in South America in the SASOL plants. These plants used an iron-based catalyst and produce gasoline and waxes by gasifying a somewhat low-grade coal to produce a synthesis gas for feed to the Fischer-Tropsch reactors.

Research continues in this area because of the potential for converting low value feedstocks into higher value products.

The chemistry of the Fischer-Tropsch reactions is, in a gross sense, quite simple. The overall reactions for the production of alkanes (No. 1), alkenes (No. 2) and alcohols (No. 3) are as follows:

1. $\begin{cases} (2n+1)H_2 + nCO \longrightarrow C_nH_{2n+2} + nH_2O \\ (n+1)H_2 + 2nCO \longrightarrow C_nH_{2n+2} + nCO_2 \end{cases}$ 2. $\begin{cases} 2nH_2 + nCO \longrightarrow C_nH_{2n} + nH_2O \\ nH_2 + 2nCO \longrightarrow C_nH_{2n} + nCO_2 \end{cases}$ 3. $\begin{cases} 2nH_2 + nCO \longrightarrow C_nH_{2n+1}OH + (n-1)H_2O \\ (n+1)H_2 + (2n-1)CO \longrightarrow \\ \quad C_nH_{2n+1} + OH + (n-1)CO_2 \end{cases}$ The types and amount of products obtained via such reactions are typically dependent upon the reaction conditions and choice of catalyst.

Few of the catalysts used in the past have been either very selective or very active. Those catalysts that were selective or active were uneconomic for other reasons, e.g., sensitivity to sulfur poisoning, or used high cost catalytic metals, such as ruthenium.

The catalyst of the present invention is iron-carbon-based. Because of the method of its preparation, the catalyst has high selectivity and/or conversion at reaction conditions considered to be quite moderate.

As noted above in the historical discussion, iron-bearing catalysts were among the first ever used in the Fischer-Tropsch reaction. Indeed, Fischer and Tropsch believed that carbides were an intermediate in the overall reaction. Later kinetics work suggested carbides could not be an intermediate in the process. Hall, et al., J. Soc. Chem. Ind., London, 65, 128 (1946); Weller, J. Amer. Chem. Soc., 69, 2432 (1947); and Kummer, et al., J. Am. Chem. Soc., 70, 3632 (1948). However, the reduced metallic iron, as used in the Lurgi-Ruhrchemie fixed bed process, appears to change from the original $\alpha$-Fe phase to a mixture of $\alpha$-Fe, $Fe_3O_4$, FeC and $Fe_2C$ as conversion operations continue. See, Malan, et al., Brennstoff-Chem., 42, 209–212 (1961).

The present invention, as will be discussed below in greater detail, involves the use of a laser to pyrolize low valence iron-carbon bearing compounds to produce a fine particle iron-carbon containing catalyst. At least a portion of the catalyst is the iron carbide, cementite.

Others have described the use of iron-carbon containing catalysts produced by laser pyrolysis in fischer-Tropsch reactions. The work of Gupta, et al. (in U.S. Pat. No. 4,468,474, issued Aug. 28, 1984) and in SPIE 458, Appl. of Lasers to Industrial Chemistry, 131–139 (1984) shows the production of iron, carbon and silicon-containing catalysts by a laser and the catalysts' subsequent use in the Fischer-Tropsch process. Moderate activity and high $C_2$–$C_4$ olefin selectivity is asserted for the catalysts.

Applicants' catalysts contain substantially no silicon.

No known prior art is believed to show the use of the catalyst described below in the efficient production of heavy hydrocarbons.

SUMMARY OF THE INVENTION

This invention deals with the production of heavier hydrocarbons, typically olefins and paraffin waxes, by using an iron-carbon catalyst which is produced by pyrolyzing a volatile iron-carbon-containing compound, optionally in the presence of an additional carbon containing compound, with a laser. The catalyst so produced may have added to it an alkali or alkaline earth metal promoter in the amount of greater than about 2% by weight.

The invention involves those catalysts and processes using those catalysts in a Fischer-Tropsch reaction to produce $C_{2}+$ aliphatic hydrocarbons, either olefins, i.e., $C_2$–$C_{15}$, ($C_2$ to $C_4$, preferably), or heavy, i.e., $C_5+$ or $C_{20}+$, hydrocarbons from CO and $H_2$.

BRIEF DESCRIPTION OF THE DRAWING

The drawing is a schematic representation of the laboratory device used to prepare the inventive catalyst used in the Examples.

DESCRIPTION OF THE PREFERRED EMBODIMENTS

Figure 1:
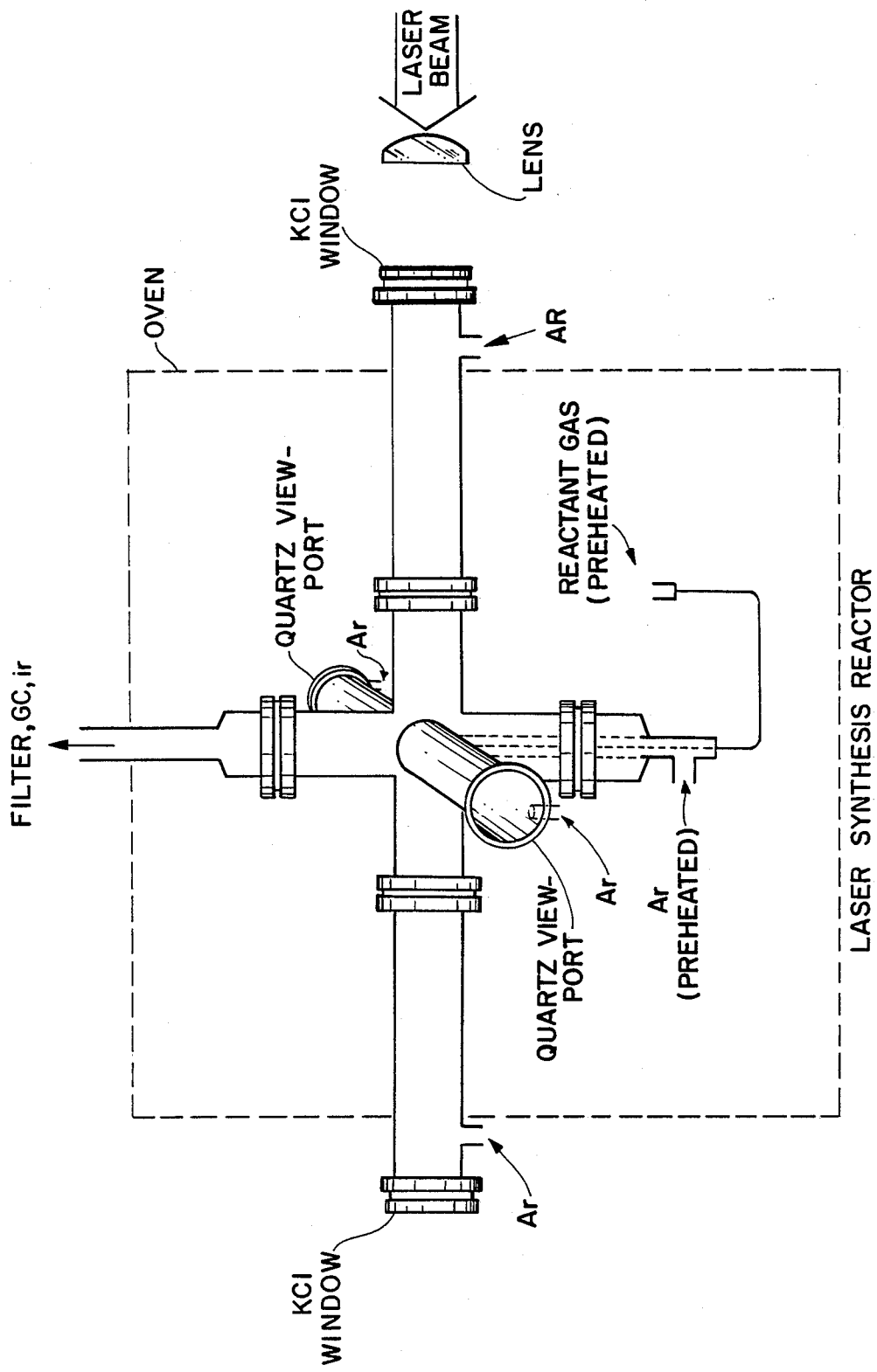

The catalyst used in the present invention is a finely divided catalyst composition comprising iron and carbon, at least a portion of which is the iron carbide cementite. The catalyst is active in the production of olefins from CO and $H_2$ and when mixed with an alkali or alkali earth promoter produces a product mixture having substantial $C_{20}+$ alkanes (waxes).

The basic iron-carbon catalyst composition used in the instant invention is disclosed and claimed in the parent cases, i.e., U.S. Ser. Nos. 735,768 and 735,769, both filed May 20, 1985. The basic catalyst may be prepared by gas phase pyrolytic decomposition of a volatile organic iron-containing compound (optionally in the presence of an additional carbon source) in the presence of a laser emission under conditions of laser power adsorption, reactant and/or diluent flow rate and pressure to produce finely divided iron-carbon containing catalyst particles.

The organic-iron-containing compounds generally are iron carbonyls. Compounds such as $Fe(CO)_5$, ferrocene, and iron acetylacetonate are all suitable; $Fe(CO)_5$ is especially preferred. The optional carbon source may act only as a diluent, depending upon reaction conditions, or may add a source of carbon to the pyrolysis reaction. The preferred carbon sources are short chain olefins, such as ethylene. Obviously, at least one of the components must absorb the radiated laser energy.

The partial pressure of the organic-iron-containing compounds depends upon the total pressure of the reactor but may be in the range of 20 to 500 torr, the optional carbon source may be 20 to 500 torr, and a diluent, such as argon or other noble gas, may be included to bring the overall system pressure to a total of 200 to 1000 torr.

By "finely divided" Fe-C catalyst particles is meant those having average diameters between 1 and 100 nm, preferably 10–50 nm. The materials usually have a BET surface area of 15 to 50 $m^2$/gm, preferably 20–35 $m^2$/gm. The iron-carbon catalyst is at least a major portion cementite, $Fe_3C$. The catalyst is a mixture of phases and, in addition to the cementite, includes $\alpha$ and $\gamma$ phase iron. The surface iron of the as-produced catalyst is carbidic. The $\alpha$ and $\gamma$-Fe phases appear to be embedded in the cementite. In some cases, the varying phases appear to be more than a simple physical mixture and may constitute a non-equilibrium mixture. A minimum amount of carbonaceous material is present on the exterior surface of the catalyst as a coating. The coating acts as a moderate passivating agent. No hydrogen pretreatment is needed to activate the as-produced base catalyst. The catalyst is not pyrophoric. The catalyst contains less than about 1.0% oxygen and is substantially bereft of silicon. Although the method of producing this catalyst is believed, of itself, to produce a catalyst which is unique, the catalyst desirably contains no more than about 20% total carbon, preferably no more than about 12% total carbon, and most desirably between about 8% and 12% total carbon. Directionally, the higher the percentage of excess matrix carbon, the lower the amount of $C_{10}$ olefins produced.

The catalyst which has been found to be optimum for the preparation of the desired heavier hydrocarbons contains at least 2% alkali or alkaline earth metal, preferably from 2% to 10% by weight.

The laser used in preferably a continuous wave (cw) type capable of producing a flux of about 200 to 10,000 W/$cm^2$ in the reaction zone and further capable of resonant absorption with a substance in the reaction zone. A $CO_2$ laser of adequate size is desirable. The residence time of the reactants in the laser beam zone should be between 1 and 60 milliseconds. The quench rate for the products leaving the zone should be such that the total time the reactant/products are at the elevated temperature is 0.15 seconds or less. Quenching may be provided mainly by radiative energy loss from the reaction products.

It is to be understood that the reactor pressures and gas flow rates described herein are not critical to the synthesis of the base catalyst, but are merely convenient for the particular reactor design employed. The only requirements are that the operating conditions be such that the time scale of the reaction be short enough to prevent deposition of excess carbon on the solid particles produced in the reaction, and that temperatures sufficient to drive the reaction be reached. Depending upon the power of the particular laser used to drive the reaction and the design of the particular reactor used to conduct the synthesis, a wide-range of reactor pressures and gas flow rates will allow preparation of the catalyst.

By changing the reaction conditions, it is possible to obtain other products from the same reactants. For example, increasing the $Fe(CO)_5$:$C_2H_4$ ratio to 1:4, while maintaining the same laser power, yields a product which is substantially all free iron and pyrophoric. Decreasing the residence time of the reactants in the laser beam has substantially the same effect. Similarly, increasing the laser power, or otherwise raising the reaction temperature, increases the carbon content of the product by continued decomposition of $C_2H_4$ after the $Fe(CO)_5$ is depleted. An increase in reaction time would have a similar effect.

The iron-carbon catalyst particles may be used as is to produce olefins; e.g., in an appropriate slurry reactor, or may be supported in one fashion or another as known in the art. The catalyst may be integrated with known supports to produce a larger catalyst matrix which may be handled with more ease.

Promoters such as alkali metals, preferably potassium or alkaline earth metals, such as magnesium, may be added using known methods. For instance, up to 10% potassium, preferably 2%, may be added to the as-produced Fe-C catalyst by impregnation with an aqueous solution of a potassium salt, such as potassium carbonate. More difficultly soluble materials may be ground and mulled with the as-produced Fe-C catalyst prior to compaction step, such as pilling, tableting or extruding.

Of course, for certain applications the iron carbide catalytic material may be placed on a refractory support, such as alumina, silica, mullite, diatomaceous earth, silica-alumina co-mixtures, or other materials known to provide high surface area.

The process for conversion of $CO/H_2$ to the various hydrocarbon products using the catalyst discussed above may be a fixed bed, or preferably a slurry process. In the slurry process the catalyst is suspended in a liquid hydrocarbon and the $CO/H_2$ mixture forced through the catalyst slurry allowing good contact between the $CO/H_2$ and the catalyst to initiate and maintain the hydrocarbon synthesis process. The slurry process is described in detail in such articles as Catal. Rev.—Sci. Engr., 21, 1980, page 225 (Kolbel, Ralek).

Advantages of a slurry process over that of a fixed bed process include better control of the exothermic heat produced in the Fischer-Tropsch process during the reaction and better control over catalyst activity maintenance by allowing continuous recycle, recovery and rejuvenation procedures to be implemented. The slurry process can be operated in a batch or in a continuous cycle, and in the continuous cycle the entire slurry can be circulated in the system, allowing for better control of the primary products residence time in the reaction zone.

The slurry liquid used in the process is a liquid at the reaction temperature, should be chemically inert under the reaction conditions, and should be a relatively good solvent for $CO/H_2$ and possess good slurrying and dispersing properties for the finely divided catalyst. Representative classes of organic liquids which can be utilized are high boiling paraffins, aromatic hydrocarbons, ethers, amines or mixtures thereof. The high boiling paraffins include $C_{10}$-$C_{50}$ linear or branched paraffinic hydrocarbons; the aromatic hydrocarbons include $C_7$-$C_{20}$ single ring and multi- and fused ring aromatic hydrocarbons; the ethers include aromatic ethers and substituted aromatic ethers where the ether oxygen is sterically hindered from being hydrogenated; the amines include long chain amines which can be primary, secondary or tertiary amines, wherein primary amines preferably contain at least a $C_{12}$ alkyl group in length, secondary amines preferably contain at least two alkyl groups being $C_7$ or greater in length, and tertiary amines preferably contain at least three alkyl groups being $C_6$ or higher in length. Representative examples of specific liquid slurry solvents useful are dodecane, tetradecane, hexadecane, octadecane, cosane, tetracosane, octacosane, dotriacontane, hexatritacosane, tetracontane, tetratetracontane, toluene, o-, m-, and p-xylene, mesitylene, $C_1$-$C_{12}$ mono- and multi-alkyl substituted benzenes, dodecylbenzene, naphthalene, anthracene, biphenyl, diphenylether, dodecylamine, di-nonylamine, trioctylamine, and the like. Preferred liquid hydrocarbon slurry solvent is octacosane or hexadecane.

The amount of catalyst used in the liquid hydrocarbon slurry solvent is generally about 10 to 60 g of dry catalyst per 500 g slurry liquid. Preferably about 30 to 50 g dry catalyst per 500 g slurry liquid slurry is utilized, being in about a respective 5:1 to 10:1 weight ratio.

The slurry system, comprised of the slurry liquid and finely divided catalyst, is generally stirred to promote good dispersion during the pretreatment in the process to avoid catalyst settling and to eliminate mass transport limitations between the gas and liquid phases.

The operating conditions for this process are generally as found below.

|  | Fixed Bed | Slurry |
|---|---|---|
| Temperature °C. | | |
| (Heavy Hydrocarbons) | 200–250 | 200–250 |
| (Preferred) (Heavy Hydrocarbons) | 220–240 | 220–240 |
| (Light Olefins) | 240–300 | 240–280 |
| (Preferred) (Light Olefins) | 250–275 | 250–275 |
| Pressure - psig | | |
| (Heavy Hydrocarbons) | 50–500 | 50–500 |
| (Preferred) (Heavy Hydrocarbons) | 150–500 | 150–500 |
| (Light Olefins) | 50–200 | 50–200 |
| (Preferred) (Light Olefins) | 50–120 | 50–120 |
| $H_2/CO$ | 0.5–9:1 | 0.5–9:1 |
| (Preferred) | 1.8–2.5:1 | 1.8–2.5:1 |
| SHSV (Volume fresh gas/ volume catalyst/hr) | 100–10,000 | 100–10,000 |
| Stirrer Speed (rpm) | — | 600–4000 |
| Recycle Gases | $C_4^-/CH_4/CO_2$ | $C_4^-/CH_4/CO_2$ |
| Diluent Gases | $N_2/Ar/CH_4/$ light hydrocarbons/$CO_2$ | $N_2/Ar/CH_4/$ light hydrocarbons/$CO_2$ |

A magnetically stabilized fluidized bed as is described in U.S. Pat. No. 4,115,927 is also suitable for this reaction.

Having thus described the invention, the following are Examples which illustrate the various workings of it. They are not intended to limit the invention in any way.

EXAMPLE 1

The base catalyst was prepared in a high surface area, low excess carbon form by a gas phase pyrolytic decomposition reaction driven by a cw $CO_2$ laser. The reactants were $Fe(CO)_5$ and $C_2H_4$. The $C_2H_4$ also served to absorb energy from the laser beam, allowing rapid heating of the reactants to reaction temperature. Post-reaction quenching is also very rapid, preventing extensive decomposition of the $C_2H_4$ on the catalyst particules and thus minimizing excess carbon content of the solid.

The reactor is shown in FIG. 1. It was constructed around a mini-flange six-way cross. As shown in the FIGURE, the vertical axis of the apparatus was used for introduction of the reactants and take-off of products. One horizontal axis was used for passage of the laser beam, while the remaining horizontal axis was used for monitoring the reaction. Argon inlets were provided near each of the four windows to prevent deposition of particulates on the windows. The $C_2H_4/Fe(CO)_5$ mixture entered the cell through a tube which was concentric with a slightly larger tube to a point 1–4 mm below the laser beam. The outer tube was used to provide an argon stream surrounding the reactant stream, thereby promoting stable flow of the reactants into the laser beam.

The laser was operated in a cw mode on the 10 P(20) line at 944 cm$^{-1}$. Although not resonant with the 950 cm$^{-1}$ Q-branch of $C_2H_4$, this line is absorbed strongly enough by weaker $C_2H_4$ adsorption bands to drive the pyrolytic reaction. The laser produced about 150 W in a beam focused to 6 mm diameter at the reaction zone, yielding a flux of 500 W/cm$^2$.

The synthesis was conducted at a reactor pressure of about 300 torr. The total argon flow to the four cell windows was about 70 SCCM (cc/min @ STP), while the argon flow coaxial to the reactants was also 70 SCCM. The $C_2H_4/Fe(CO)_5$ mixture was provided by bubbling $C_2H_4$ through liquid $Fe(CO)_5$ held at ambient temperature (23° C.) where the vapor pressure is 25 torr. [Gilbert, A. G.; Sulzmann, K. P., *J. Electrochem. Soc.*, 1974, 121, 832–834]. The $C_2H_4$ flow rate was about 6 SCCM. Since the $Fe(CO)_5$ will essentially attain its equilibrium vapor pressure in the $C_2H_4$ stream under these flow conditions, the ratio of the reactants in the gas stream is determined by the total reactor pressure; $C_2H_4:Fe(CO)_5 = (300-25):25 = 11:1$.

The laser-driven reaction gave a bright yellow flame, indicating that quite high temperatures were obtained. Under the flow and pressure conditions given above, the residence time of the reactants in the laser beam is 25–40 ms and the quenching rate should be fast enough to keep the total time at high temperature, e.g., above about 500° C., to 0.1 s or less.

The solid products were collected on an 0.5 μm-pore Teflon membrane filter. The gaseous products were monitored by gas chromatograph (gc) and infrared detector (ir). The ir showed that conversion of $Fe(CO)_5$ to products was quantitative under reaction conditions. The characteristic 2 (CO) bands of $Fe(CO)_5$ could not be seen in the product gases, though free CO was present. The gc showed that most of the $C_2H_4$ did not react. The gas yields were to some extent dependent upon the linear flow rate of the reactant stream at the laser beam as shown below. Since the reactant stream does undergo some spreading as it enters the reactor, the linear velocity decreases with distance from the inlet tip. Raising the laser beam further above the inlet tip, or alternatively, decreasing the flow rate of the reactants, led to increased residence time of the reactants in the beam. The gas yields then indicated higher reaction temperature, or a longer reaction, or both, as demonstrated by the increase in yields of $C_2H_2$ and $CH_4$ relative to $C_2H_4$.

| | Measured Mole %, TCD | |
| Gas | High Flow | Low Flow |
| --- | --- | --- |
| $C_2H_4$ | 64 | 57% |
| CO | 32 | 29% |
| $C_2H_2$ | 3.3 | 12.5% |
| $CO_2$ | 0.67 | 0.08% |
| $CH_4$ | 0.50 | 1.55% |

$H_2$ was also observed, but the peak area is not meaningful (He carrier). A peak for the $C_2H_6$ could be observed by eye in the gc trace, but was so weak and broad that the integrator normally did not detect it. The yield was measured at 0.06% of the gases in one instance.

The analysis of one sample of solid prepared by the above method was: Fe, 86.2%; C, 12.74%; O, 1.73%; H, <0.35%. X-ray diffraction showed that the major phase present was $Fe_3C$. The BET surface area was 27 m²/g, and XPS showed that the surface was carbon rich, with only Fe and C present. The catalyst so prepared was not pyrophoric and did not appear to oxidize significantly in air. Analysis by Mossbauer spectroscopy showed that $Fe_3C$ was the major phase, with smaller amounts of α-Fe and α-Fe also present.

EXAMPLE II

Gas streams containing $Fe(CO)_5/C_2H_4$ were pyrolyzed using the method of Example I, with a cw $CO_2$ laser producing about 200 W, to yield powders containing Fe and C. The total pressure of the reactant gases was 385 torr. The partial pressure of $Fe(CO)_5$ and the flow rate of the $C_2H_4$ were varied. Analytical results for the powders are shown below.

| Synthesis | (a) | (b) | (c) | (d) |
| --- | --- | --- | --- | --- |
| $Fe(CO)_5$ partial pressure, torr | 92 | 73 | 73 | 30 |
| $C_2H_4$ flow rate, ccm | 15 | 15 | 35 | 35 |
| Powder Analysis, % Fe | 92.9 | 90.9 | 89.6 | 87.0 |
| Powder Analysis, % C | 8.15 | 9.04 | 8.60 | 10.80 |
| Powder Surface Area, m²/g | 20.4 | 22.2 | 24.1 | 34.8 |

All powders were shown to be mainly $Fe_3C$ by x-ray diffraction.

These results demonstrate that the powder composition can be controlled by varying the preparation conditions.

EXAMPLE III

Catalyst (1):

Samples of $Fe_3O_4$ were reduced in flowing $H_2$ at 450° C. for 5 to 7 hours and then treated in $H_2/CO$ at 350° C. until the x-ray diffraction pattern indicated that all the iron was converted to a carbide phase, predominantly of the form $Fe_5C_2$ and $Fe_3C$ in a matrix of 40 to 70 weight percent of an amorphous carbon phase. This catalyst was transferred directly to the reactor and brought up to reaction temperature and pressure under a $CO/H_2$ mixture.

Catalyst (2):

A gas stream containing $Fe(CO)_5/C_2H_4$ was pyrolyzed using the method of Example I with a cw $CO_2$ laser to yield a powder containing Fe and C as the only detectable components with 5 to 15 weight percent of an amorphous carbon phase.

The performance of these two catalysts under continuous stirred tank reactor conditions is shown below.

| Catalyst | (1) | (2) |
| --- | --- | --- |
| v/v cat/hr | 2000 | 4000 |
| % CO Conversion | 71.9 | 82.5 |
| Wt. % Selectivity ($CO_2$ Free Basis) | | |
| $CH_4$ | 16.1 | 9.5 |
| $C_2°$ | 9.7 | 5.4 |
| $C_2=$ | 3.0 | 7.5 |
| $C_3°$ | 5.6 | 1.3 |
| $C_3=$ | 10.9 | 10.5 |
| $C_4°$ | 3.0 | 1.1 |
| $C_4=$ | 5.0 | 9.0 |
| % Olefin in $C_2$–$C_4$ | 50.7 | 77.6 |

Conditions: 270° C., 2/1 $H_2/CO$, 200 SCCM, 75 psi, octacosane, solvent, 600 rpm. The $H_2/CO$ mixture was run directly through the reactor without recycle of product gases.

The results demonstrate the high activity and olefin selectivity provided by the laser generated Fe-C catalyst (2) relative to the conventionally prepared iron carbide catalyst (1).

EXAMPLE IV

Catalyst (3):

Samples of the laser generated Fe/C catalyst (2) of the instant invention were treated with $H_2/CO$ at 350° C. to generate an amorphous carbon phase equivalent to that present in the conventionally prepared iron carbide catalyst (1).

The performance of the $H_2/CO$ treated laser generated Fe/C catalyst relative to the conventional iron carbide catalyst (1) is shown below.

| Catalyst | (1) | (3) |
|---|---|---|
| v/v cat/hr | 2000 | 5000 |
| % CO Conversion | 71.9 | 33.0 |
| Wt. % Selectivity ($CO_2$ Free Basis) | | |
| $CH_4$ | 16.1 | 11.1 |
| $C_2°$ | 9.7 | 7.3 |
| $C_2=$ | 3.0 | 16.6 |
| $C_3°$ | 5.6 | 1.0 |
| $C_3=$ | 10.9 | 9.0 |
| $C_4°$ | 3.0 | 0.6 |
| $C_4=$ | 5.0 | 6.6 |
| % Olefin in $C_2$-$C_4$ | 50.7 | 80.0 |
| % Olefin in $C_{10}+$ | N/A | 35.0 |

Conditions: 270° C., 2/1 $H_2/CO$, 200 SCCM, 75 psi, octacosane solvent, 600 rpm.

These results show the improved olefin selectivity achieved with the laser generated Fe/C catalyst (3) that contains amorphous carbon at levels found in the conventional iron carbide synthesis catalyst (1).

EXAMPLE V

Catalyst (4):

A laser synthesized Fe/Si/C composition analogous to that described by Gupta and Yardley was prepared by cw $CO_2$ laser pyrolysis of $Fe(CO)_5/C_2H_4/SiH_2(CH_3)_2$.

The behavior of this material relative to the Si-free catalyst (2) of the invention is shown below.

| Catalyst | (2) | (4) |
|---|---|---|
| v/v cat/hr | 4000 | 500 |
| % CO Conversion | 82.5 | 5.0 |
| Wt. % Selectivity ($CO_2$ Free Basis) | | |
| $CH_4$ | 9.5 | 15.9 |
| $C_2°$ | 5.4 | 6.0 |
| $C_2=$ | 7.5 | 3.0 |
| $C_3°$ | 1.3 | 15.0 |
| $C_3=$ | 10.5 | 12.0 |
| $C_4°$ | 1.1 | 6.0 |
| $C_4=$ | 9.0 | 4.0 |
| % Olefin in $C_2$-$C_4$ | 72.6 | 41.0 |

Conditions: 270° C., 2/1 $H_2/CO$, 200 SCCM, 75 psi, octacosane solvent, 600 rpm.

These results demonstrate the superior activity and selectivity provided by the Fe/C catalyst (2) of this invention relative to the Fe/Si/C catalyst (4).

EXAMPLE VI

The conventionally prepared iron carbide catalyst (1), the laser generated Fe/C (2) and Fe/Si/C (4) catalysts were examined under CSTR conditions: 270° C., 2/1 $H_2/CO$, 200 SCCM, 75 psig, octacosane solvent, 600 ppm. The yield and composition of liquid products collected at 4° C. and 15 psig were determined after 48 hours and are shown below.

| Catalyst | 1 | 2 | 4 |
|---|---|---|---|
| Wt. % $C_{10}$ ($CO_2$ Free Basis) | nil | 1.9 | nil |
| Distribution (%) | | | |
| 1-olefin | nil | 47.2 | nil |
| n-paraffin | — | 10.4 | — |
| n-alcohol | — | 1.1 | — |
| others | — | 36.5 | — |

The laser generated Fe/C catalyst (2) of this invention in contrast to the iron carbide (1) or laser generated Fe/Si/C catalyst (4) generates a recoverable $C_{10}$ fraction containing high levels of 1-olefin.

EXAMPLE VII

The laser generated Fe/C catalyst (2) was examined at 100 psig at 270° C. and 240° C. under CSTR conditions with 2/1 $H_2/CO$. The results of those tests are shown below:

| Temperature, °C. | 240 | 270 |
|---|---|---|
| v/v cat/hr | 4000 | 4000 |
| % CO Conversion | 43.9 | 89.3 |
| Wt. % Selectivity ($CO_2$ Free Basis) | | |
| $CH_4$ | 5.9 | 6.4 |
| $C_2°$ | 0.01 | 2.0 |
| $C_2=$ | 6.0 | 4.9 |
| $C_3°$ | 4.2 | 3.3 |
| $C_3=$ | 8.1 | 9.7 |
| $C_4°$ | 0.8 | 0.8 |
| $C_4=$ | 5.6 | 8.3 |
| % Olefin in $C_2$-$C_4$ | 80 | 79 |

These results demonstrate the high activity and olefin selectivity provided by the catalyst of our invention over a reasonably wide range of operating temperatures.

EXAMPLE VIII

A laser generated Fe/C catalyst made according to Example I with about 5 to 15 weight percent of amorphous carbon was impregnated with $K_2CO_3$ to yield a material containing about 2 weight percent K. This material was examined in a continuously stirred tank reactor at reaction conditions of 270° C., 2/1 $H_2/CO$, 400 v/v cat/hr, 75 psig, octacosane, 600 rpm. The results are shown below:

| % CO Conversion | 66.5 |
|---|---|
| Wt. % Selectivity ($CO_2$ Free Basis) | |
| $CH_4$ | 5.6 |
| $C_2°$ | nil |
| $C_2=$ | 3.7 |
| $C_3°$ | 0.5 |
| $C_3=$ | 4.3 |
| $C_4°$ | 0.3 |
| $C_4=$ | 3.5 |
| $C_5+$ | 82.1 |
| % Olefin in $C_2$-$C_4$ | 93.5 |

The results demonstrate the high olefin selectivity provided by the alkali promoted catalyst of our invention.

EXAMPLE IX

A mixture of 2.0 g of the laser generated Fe/C powder and 6 g of MgO were pelletized, crushed and sieved (80–150 Tyler mesh) and examined in a down flow fixed-bed reactor at 221° C., 2/1 $H_2$/CO, 3000 v/v/hr, and 75 psig.

| % CO Conversion | 45.7 |
|---|---|
| to $CO_2$ | 9.0 |
| to Hydrocarbons | 36.7 |
| Wt. % Selectivity ($CO_2$ Free Basis) | |
| $CH_4$ | 5.0 |
| $C_2$-$C_4$ | 9.0 |
| $C_5^+$ | 86.0 |
| $C_2^=/C_2^°$ | 0.7 |
| $C_3^=/C_3^°$ | 4.0 |

The results demonstrate the usefulness of the laser generated catalyst in the synthesis of $C_5+$ hydrocarbons.

EXAMPLE X

A 300 cc Parr Continuously Stirred Tank Reactor (CSTR) was charged with 8.0 g of a conventionally prepared catalyst $Fe_{4.75}C_2$/x g atom % K where x=0, 2 and 10. The material contains an additional carbon phase, ∧50 to 70 weight percent. The reactor was attentively charged with 2.0 g of a laser generated carbide catalyst $Fe_3C_y$/x g atom % K where y is from 1 to 2 and x=0 or 2.0. A slurry medium consisting of 70 g of octacosane $C_{28}H_{58}$ containing trace levels of sodium bromide, ≦300 ppm, was also charged, the system purged with a gas mixture $H_2$:CO:$N_2$, 60:30:10 molar ratio and then brought to reaction conditions: 240° C., 75 psi, 60:30:10 sccm $H_2$:CO:$N_2$ with stirring at 600 rpm. An exit gas analyzer was employed to determine the extent of CO hydrogenation, the carbon efficiency to $CH_4$ and the olefin contant of the $C_2$-$C_4$ fraction. Higher molecular weight products were analyzed off-line on completion of the experiment. Results are provided in the Table below. The high volumetric activity and good olefin selectivity of the laser generated catalyst, even with 0% K, are clearly shown.

The laser generated catalyst with about 2% K was found to provide unusually high selectivity for production of hydrocarbon wax even when compared to the Fe-Co analog with 10% K.

TABLE

| | FeCoC Cat. % olefin in | | | | FeC Cat. % olefin in | | | |
|---|---|---|---|---|---|---|---|---|
| % K | % Conv | $C_2$-$C_4$ | % $CH_4$ | % $C_5^+$ | % Conv | $C_2$-$C_4$ | % $CH_4$ | $C_5^+$ |
| 0 | 72 | 37 | 20 | 40 | 55 | 86 | 7 | 78 |
| 2 | 48 | 80 | 10 | 64 | 38 | 87 | 5 | 88 |
| 10 | 40 | 87 | 10 | 64 | — | — | — | — |

What is claimed is:

1. A process for producing $C_2+$ aliphatic hydrocarbons from a CO and $H_2$ mixture comprising the step of contacting said mixture with a catalyst comprising finely divided non-pyrophoric iron-carbon catalyst particles comprising iron and carbon, in the substantial absence of silicon, a substantial portion of which is dementite, which was produced in a reaction zone in the presence of laser radiation under such conditions of laser flux density, power adsorption, concentration of iron compound reactants selected from the group consisting of iron carbonyls, iron acetylacetonate, and ferrocene, and pressure sufficient to produce non-pyrophoric iron-carbon particles having average diameters between 1 and 100 nm.

2. The process of claim 1 wherein said catalyst is subsequently impregnated with at least one promoter selected from the group of the salts and oxides of alkali and alkaline earth metals.

3. The process of claim 2 for producing $C_5+$ hydrocarbons wherein said CO and $H_2$ mixture contacts said catalyst at a temperature between 200° C. and 250° C.

4. The process of claim 3 wherein the ratio of $H_2$:CO is between 0.5:1 and 9:1.

5. The process of claim 4 wherein the ratio of $H_2$:CO is between 1.8:1 and 2.5:1.

6. The process of claim 5 wherein the catalyst is in a slurry.

7. The process of claim 5 wherein the catalyst is in bulk.

8. The process of claim 3 wherein said temperature is between 220° C. and 240° C.

9. The process of claim 3 wherein said promoter comprises potassium.

10. The process of claim 3 wherein said promoter comprises magnesium.

11. The process of claim 3 wherein the catalyst is in a slurry.

12. The process of claim 1 for producing $C_2$-$C_{15}$ olefins wherein said CO and $H_2$ mixture contacts said catalyst at a temperature between 240° C. and 300° C.

13. The process of claim 12 wherein the ratio of $H_2$:CO is between 0.5:1 and 9:1.

14. The process of claim 13 wherein the ratio of $H_2$:CO is between 1.8:1 and 2.5:1.

15. The process of claim 14 wherein the catalyst is in a slurry.

16. The process of claim 14 wherein the catalyst is in bulk.

17. The process of claim 12 wherein said temperature is between 250° C. and 270° C.

18. The process of claim 12 wherein the catalyst is in a slurry.

19. The process of claim 12 wherein the catalyst is subsequently impregnated with at least one promoter selected from the group of the salts and oxides of alkali and alkaline earth metals.

20. The process of claim 19 wherein the promoter comprises potassium.

21. The process of claim 19 wherein the promoter comprises magnesium.

22. The process of claim 19 wherein the catalyst is in a slurry.

* * * * *